United States Patent
Ito et al.

(10) Patent No.: US 7,312,354 B2
(45) Date of Patent: Dec. 25, 2007

(54) ADAMANTANE DERIVATIVE AND PRODUCTION PROCESS FOR THE SAME

(75) Inventors: Hajime Ito, Chiba (JP); Shinji Tanaka, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 477 days.

(21) Appl. No.: 10/525,429

(22) PCT Filed: Oct. 7, 2004

(86) PCT No.: PCT/JP2004/014835

§ 371 (c)(1),
(2), (4) Date: Feb. 23, 2005

(87) PCT Pub. No.: WO2005/100304

PCT Pub. Date: Oct. 27, 2005

(65) Prior Publication Data

US 2006/0167302 A1    Jul. 27, 2006

(30) Foreign Application Priority Data

Apr. 2, 2004    (JP) .............................. 2004-109743

(51) Int. Cl.
C07C 255/03    (2006.01)
(52) U.S. Cl. ...................................... 558/428; 558/303
(58) Field of Classification Search ................ 558/303, 558/428
See application file for complete search history.

(56) References Cited

U.S. PATENT DOCUMENTS 6,054,254 A * 4/2000 Sato et al. ................... 430/322
6,472,120 B1 * 10/2002 Jung et al. ................ 430/270.1

\* cited by examiner

*Primary Examiner*—Golam M. M. Shameem
(74) *Attorney, Agent, or Firm*—Edwards Angell Palmer & Dodge LLP; Peter F. Corless

(57) ABSTRACT

Provided are an adamantane derivative characterized by having a structure represented by Formula (I) and a process for producing an adamantane derivative in which n is 0 in Formula (I) described above, wherein an adamantane compound is reacted with a nitrile compound and then with acid halide or acid anhydride of (meth)acrylic acids. The adamantane derivative characterized by having a structure represented by Formula (I) is a novel adamantane derivative which is useful as a monomer for functional resins such as a photosensitive resin in the photolithograpy field, and it can efficiently be produced by the production process described above

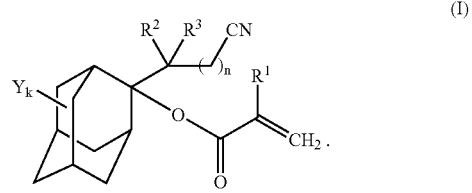

(I)

5 Claims, No Drawings

ADAMANTANE DERIVATIVE AND PRODUCTION PROCESS FOR THE SAME

BACKGROUND OF THE INVENTION

The present invention relates to a novel adamantane derivative and a production process for the same, more specifically to nitrile group-containing adamantyl (meth) acrylates useful as a monomer for functional resins such as a photosensitive resin in the photolithograpy field and a process for efficiently producing the same.

RELATED ART

It is known that adamantane is a stable compound having a structure in which four cyclohexane rings are condensed in a cage form and having a high symmetric property and that the derivatives thereof are useful as a medical raw material and a raw material for high functional industrial materials because they show specific functions. They have, for example, optical characteristics and a heat resistance, and therefore it is tried to use them for an optical disc substrate, an optical fiber and a lens (patent document 1 and patent document 2).

Further, it is tried to use adamantane esters as a resin raw material for a photoresist making use of an acid-sensitivity, a dry etching resistance and a UV ray transmittance thereof (patent document 3).

On the other hand, as fining of a semiconductor element proceeds in recent years, it is required to be further fined at a lithography step in the production thereof, and therefore investigated are various methods for forming fine patterns using photoresist materials corresponding to irradiated beams having a short wavelength such as KrF, ArF and $F_2$ eximer laser beams. A novel photoresist material which can correspond to irradiated beams having a short wavelength such as the eximer laser beam and the like described above is desired to be developed.

Disclosed as a photoresist material is, for example, a chemically sensitive type photoresist material which comprises an acid-sensitive polymer having an alkali-soluble group protected by a protective group and having a structural unit eliminating the protective group described above by an acid to make the polymer alkali-soluble and an acid-generating agent releasing an acid by irradiation with a radiation and in which a nitrile group-containing organic group is introduced into the protective group described above in order to enhance an adhesive property with a substrate (patent document 4). In this patent document 4, cyclic hydrocarbon group is shown as the preferred protective group into which a nitrile group-containing organic group is introduced. However, specific examples using an adamantane derivative into which a nitrile group-containing organic group is introduced and which has a (meth)acryloyloxy group are not shown at all in the examples.

Patent document 1: Japanese Patent Application Laid-Open No. 305044/1994
Patent document 2: Japanese Patent Application Laid-Open No. 302077/1997
Patent document 3: Japanese Patent Application Laid-Open No. 39665/1992
Patent document 4: Japanese Patent Application Laid-Open No. 352694/1999

DISCLOSURE OF THE INVENTION

The present invention has been made under such circumstances, and an object thereof is to provide an adamantane derivative useful as a monomer for functional resins such as a photosensitive resin in the photolithograpy field and a production process for the same.

Intensive researches repeated by the present inventors in order to achieve the object described above have resulted in finding that nitrile group-containing adamantyl (meth)acrylates having a specific structure can sufficiently be suited to the object described above and that the above compounds can efficiently be produced by carrying out reaction using corresponding adamantanone compounds as a raw material. The present invention has been completed based on such knowledge.

That is, the present invention provides:

(1) an adamantane derivative characterized by having a structure represented by Formula (I):

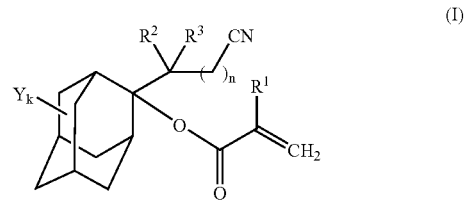

wherein $R^1$ represents a hydrogen atom, methyl or trifluoromethyl; Y represents an alkyl group having 1 to 10 carbon atoms, a halogen atom, a hydroxyl group or =O formed by combining two Y, and plural Y may be the same or different; $R^2$ and $R^3$ represent a hydrogen atom or an alkyl group having 1 to 10 carbon atoms; k represents an integer of 0 to 14; n represents an integer of 0 to 3; and $R^2$ and $R^3$ may be the same or different, (2) the adamantane derivative as described in the above item (1), wherein n is 0 in Formula (I) described above, (3) a production process for an adamantane derivative represented by Formula (I-a):

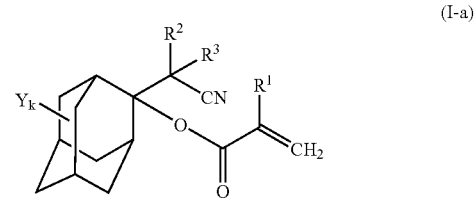

(wherein $R^1$, $R^2$, $R^3$, Y and k are the same as those described above), characterized by reacting adamantanes represented by Formula (II):

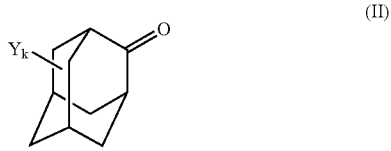

(wherein Y represents an alkyl group having 1 to 10 carbon atoms, a halogen atom, a hydroxyl group or =O formed by combining two Y; k represents an integer of 0 to 14; and plural Y may be the same or different) with a nitrile compound represented by Formula (III):

(III)

(wherein $R^2$ and $R^3$ represent a hydrogen atom or an alkyl group having 1 to 10 carbon atoms; and $R^2$ and $R^3$ may be the same or different) in the presence of a base and then with acid halide or acid anhydride of (meth)acrylic acids represented by Formula (IV):

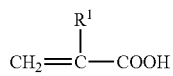
(IV)

(wherein $R^1$ represents a hydrogen atom, methyl or trifluoromethyl), (4) a production process for an adamantane derivative represented by Formula (I):

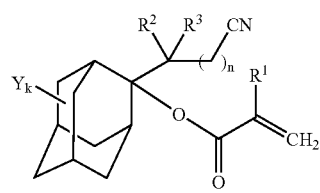
(I)

(wherein $R^1$, $R^2$, $R^3$, Y, k and n are the same as those described above), characterized by subjecting adamantanes represented by Formula (II):

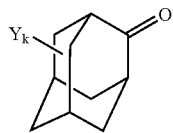
(II)

(wherein Y represents an alkyl group having 1 to 10 carbon atoms, a halogen atom, a hydroxyl group or =O formed by combining two Y; k represents an integer of 0 to 14; and plural Y may be the same or different) to Grignard reaction with a nitrile compound represented by Formula (V):

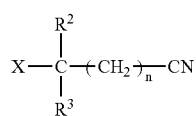
(V)

(wherein $R^2$ and $R^3$ represent a hydrogen atom or an alkyl group having 1 to 10 carbon atoms; X represents a halogen atom; n represents an integer of 0 to 3; and $R^2$ and $R^3$ may be the same or different) and then reacting it with acid halide or acid anhydride of (meth)acrylic acids represented by Formula (IV):

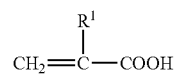
(IV)

(wherein $R^1$ represents a hydrogen atom, methyl or trifluoromethyl) and (5) the production process for an adamantane derivative as described in the above (4), wherein n is 0 in the nitrile compound represented by Formula (V).

BEST MODE FOR CARRYING OUT THE INVENTION

The adamantane derivative of the present invention is the compound represented by Formula (I), and the compound and the production process for the same shall be explained below.

The compound of the present invention is nitrile group-containing adamantyl (meth)acrylates having a structure represented by Formula (I):

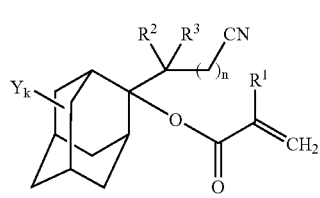
(I)

In Formula (I) described above, $R^1$ represents a hydrogen atom, methyl or trifluoromethyl, and Y represents an alkyl group having 1 to 10 carbon atoms, a halogen atom, a hydroxyl group or =O formed by combining two Y. In this case, plural Y may be the same or different. $R^2$ and $R^3$ represent a hydrogen atom or an alkyl group having 1 to 10 carbon atoms; k represents an integer of 0 to 14; and n represents an integer of 0 to 3. $R^2$ and $R^3$ may be the same or different.

In the formula described above, the alkyl group having 1 to 10 carbon atoms in Y, $R^2$ and $R^3$ may be any of the linear, branched and cyclic groups, and capable of being given are, for example, methyl, ethyl, various propyls, various butyls, various pentyls, various hexyls, various heptyls, various octyls, various nonyls, various decyls, cyclopentyl and cyclohexyl. The above alkyl groups may be substituted with a halogen atom, a hydroxyl group and the like. The case in which n is 0 is preferred. Fluorine, chlorine, bromine and iodine can be given as the halogen atom represented by Y.

Capable of being given as the particularly preferred compound represented by Formula (I) are, for example, 2-cyanomethyl-2-adamantyl acrylate, 2-(1-cyanoethyl)-2-adamantyl acrylate, 2-(1-cyanopropyl)-2-adamantyl acrylate, 2-(1-cyano-2-methylpropyl)-2-adamantyl methacrylate, 2-cyanomethyl-2-adamantyl methacrylate, 2-cyanomethyl-2-adamantyl methacrylate, 2-(1-cyanoethyl)-2-adamantyl methacrylate, 2-(1-cyanopropyl)-2-adamantyl methacrylate, 2-cyanomethyl-3-chloro-2-adamantyl acrylate, 2-cyanomethyl-4-oxo-2-adamantyl methacrylate and 2-cyanomethyl-perfluoro-2-adamantyl acrylate.

Next, the preferred production process for the adamantane derivative of the present invention described above shall be explained.

The preferred production process for the adamantane derivative of the present invention has two embodiments of a production process 1 and a production process 2.

In the production process 1, the adamantane derivative is obtained by reacting the adamantanes represented by Formula (II) described above with the nitrile compound represented by Formula (III) described above in the presence of a base (hereinafter referred to as the first step) and then with the acid halide or the acid anhydride of the (meth)acrylic acids represented by Formula (IV) (hereinafter referred to as the second step).

The first step and the second step shall be explained in order.

(1) First Step

In the present step, acetonitrile, propionitrile, butyronitrile, isobutyronitrile, valeronitrile, cyclohexylmethylnitrile and 3-methylbutyronitrile can be given as the nitrile compound represented by Formula (III) described above. A use amount of the above nitrile compound is usually 1 to 1.5 in terms of a mole ratio to the adamantanes.

In the present step, a base is usually used as a catalyst, and a solvent is used if necessary.

Capable of being given as the base are strong bases which can pull out a hydrogen atom of an α-position in a nitrile group, such as n-butyllithium, sodium hydride, lithium diisopropylamide and sodium amide. The above catalysts may be used alone or in combination of two or more kinds thereof.

Used as the solvent is a solvent which is stable against the base and in which a solubility of the adamantanes which are the raw material is 0.5 mass % or more, preferably 5 mass % or more at the reaction temperature. An amount of the solvent is such an amount that the adamantanes have a concentration of 0.5 mass % or more, preferably 5 mass % or more in the reaction mixture. In this case, the adamantanes may stay in a suspension state but is preferably dissolved. Moisture contained in the solvent is preferably removed before use. To be specific, capable of being given are hydrocarbon base solvents such as n-hexane, n-heptane and the like and ether base solvents such as diethyl ether, tetrahydrofuran and the like. The above solvents may be used alone or in combination of two or more kinds thereof.

The reaction temperature is used usually in a range of −200 to 200° C. If it falls in the above range, the reaction rate shall not be reduced, and the reaction time shall not be extended too much. Further, by-production of a polymer shall not grow large. The reaction temperature falls preferably in a range of −80 to 100° C.

The reaction pressure is used in a range of 0.01 to 10 MPa in terms of an absolute pressure. If the reaction pressure falls in the above range, a specific pressure proof apparatus is not required, and therefore it is economical. The reaction pressure falls preferably in a range of an atmospheric pressure to 1 MPa.

The reaction time falls in a range of usually one minute to 24 hours, preferably 10 minutes to 6 hours.

In the first step, an alkoxide matter of nitrile group-containing adamantanols (hereinafter referred to merely as the alkoxide matter) is usually obtained. The above matter may be neutralized with an acid and turned into an alcohol matter, and it is isolated for use in the second step. It is simpler and more preferred to use the alkoxide matter as it is in the second step or use the alcohol matter in the second step without isolating.

(2) Second Step

In the reaction of the alkoxide matter produced in the first step with the acid halide or the acid anhydride of (meth)acrylic acids, a solution of the acid halide or the acid anhydride of (meth)acrylic acids may be added to a solution of the alkoxide matter or a solution of the alkoxide matter may be added to a solution of the acid halide or the acid anhydride of (meth)acrylic acids, and the latter is preferred. The acid anhydride is preferred to the acid halide.

A mole ratio of the acid halide or the acid anhydride of (meth)acrylic acids to the alkoxide matter is usually 0.8 to 10, and if it falls in the above range, a yield of the final product is elevated. The ratio falls preferably in a range of 0.9 to 3.

In the present step, a base is usually used as a catalyst, and a solvent is used if necessary.

Capable of being given as the base are sodium amide, triethylamine, tributylamine, trioctylamine, pyridine, N,N-dimethylaniline, 1,5-diazabicyclo-[4.3.0]nonene-5 (DBN), 1,8-diazabicyclo[5.4.0]undecene-7 (DBU), sodium hydroxide, potassium hydroxide, sodium hydride, potassium carbonate, silver oxide, sodium methoxide and potassium t-butoxide. The above bases may be used alone or in combination of two or more kinds thereof.

A solvent in which a solubility of the alkoxide matter is 0.5 mass % or more, preferably 5 mass % or more at the reaction temperature is used as the solvent. In this case, the alkoxide matter may stay in a suspension state but is preferably dissolved. Moisture contained in the solvent is preferably removed before use. To be specific, capable of being given are hydrocarbon base solvents such as n-hexane, n-heptane and the like, ether base solvents such as diethyl ether, tetrahydrofuran and the like, halogen base solvents such as dichloromethane, carbon tetrachloride and the like, dimethylsulfoxide and N,N-dimethylsulfoxide. The above solvents may be used alone or in combination of two or more kinds thereof.

When the alkoxide matter obtained in the first step is used as it is in the second step or when it is turned into an alcohol matter to use the above alcohol matter in the second step without isolating, the same solvent as used in the first step is preferably used.

The reaction temperature is used usually in a range of −200 to 200° C. If it falls in the above range, the reaction rate shall not be reduced, and the reaction time shall not be extended too much. Further, by-production of a polymer shall not grow large. The reaction temperature falls preferably in a range of −80 to 100° C.

The reaction pressure is used in a range of 0.01 to 10 MPa in terms of an absolute pressure. If the reaction pressure falls in the above range, a specific pressure proof apparatus is not required, and therefore it is economical. The reaction pressure falls preferably in a range of an atmospheric pressure to 1 MPa.

The reaction time falls in a range of usually one minute to 24 hours, preferably 10 minutes to 6 hours.

After finishing the reaction, the salts are removed by washing with water, and then the unreacted nitrile group-containing adamantanols are deposited by a poor solvent such as n-hexane and removed to refine the intended compound.

Distillation, crystallization and column separation can be used for refining and separation of the intended compound, and they can be selected according to the physical properties of the compound and the kind of impurities. Thus, the adamantane derivative represented by Formula (I-a) described above can be obtained.

The compound thus obtained can be identified by means of gas chromatography (GC), liquid chromatography (LC), gas chromatography mass spectrometry (GC-MS), a nuclear magnetic resonance spectral method (NMR), an infrared spectral method (IR) and a melting point-measuring apparatus.

Next, the second production process 2 shall be explained.

In the second production process 2, the adamantane derivative is obtained by subjecting the adamantanes represented by Formula (II) described above to Grignard reaction with the nitrile compound represented by Formula (III) described above (hereinafter referred to as the first step) and then reacting it with the acid halide or the acid anhydride of the (meth)acrylic acids represented by Formula (IV) described above (hereinafter referred to as the second step).

(1) First Step

In the present step, capable of being given as the nitrile compound represented by Formula (V) described above are, for example, halogenoacetonitrile, 2-halogenopropionitrile, 3-halogenopropionitrile, 2-halogenobutyronitrile, 3-halogenobutyronitrile, 4-halogenobutyronitrile, 2-halogenovaleronitrile, 3-halogenovaleronitrile, 4-halogenovaleronitrile, 5-halogenovaleronitrile, 2-halogeno-3-methylbutyronitrile, 2-cyclohexyl-2-halogenoacetonitrile and 3-cyclohexyl-3-halogenopropionitrile. Among the above compounds, halogenoacetonitrile is preferred.

A use amount of the above nitrile compound is usually 1 to 1.5 based on the adamantanes. Ether base solvents such as diethyl ether and tetrahydrofuran can be used as the solvent.

The reaction temperature is used usually in a range of −200 to 200° C. If it falls in the above range, the reaction rate shall not be reduced, and the reaction time shall not be extended too much. Further, by-production of a polymer shall not grow large. The reaction temperature falls preferably in a range of −80 to 100° C.

The reaction pressure is used in a range of 0.01 to 10 MPa in terms of an absolute pressure, and the reaction time falls in a range of usually one minute to 24 hours, preferably 10 minutes to 6 hours.

Thus, the nitrile group-containing adamantanols are obtained. The above adamantanols may be isolated and used in the second step or may be used in the second step without isolating.

(2) Second Step

The second step can be carried out in the same manner as in the production process 1 described above. In this second step, the adamantane derivative represented by Formula (I) described above is obtained. The compound thus obtained is identified by the same method as in the production process 1 described above.

EXAMPLES

Next, the present invention shall be explained in further details with reference to examples, but the present invention shall by no means be restricted by these examples.

Example 1

Synthesis of 2-cyanomethyl-2-adamantyl Methacrylate Represented by a Structural Formula

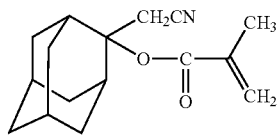

A glass reactor of 500 ml which was equipped with a stirrer and dropping funnel was charged with 100 ml of dried tetrahydrofuran, and it was cooled (−78° C.) on a dry ice/isopropanol bath and then charged with 100 ml (160 millimole) of a n-BuLi/n-hexane solution (1.6M). Acetonitrile 10 ml (192 millimole) was dropwise added thereto in 10 minutes. The solution stayed in a slurry state by a deposit. A solution obtained by dissolving 22.2 g (148 millimole) of adamantanone (Adamantanone, manufactured by Idemitsu Petrochemical Co., Ltd.) in 100 ml of tetrahydrofuran was dropwise added thereto. The deposit was slowly dissolved, and the solution became transparent. After finishing dropwise adding, the temperature was slowly elevated up to 0° C., and gas chromatographic analysis was carried out to confirm that adamantanone was completely converted to Li alkoxide of 2-cyanomethyl-2-adamantanol at a selectivity of 99.5%. This reaction liquid was dropwise added in 30 minutes to a solution of 47 ml (318 millimole) of methacrylic anhydride, 45 ml (320 millimole) of dried triethylamine and 100 ml of dried tetrahydrofuran while the solution was cooled to 0° C. on an ice and water bath. After further stirred at 0° C. for 30 minutes, 200 mol of water and 300 ml of diethyl ether were added thereto and stirred. This solution was transferred into a separating funnel of 2 liter to remove an aqueous phase, and then an organic phase was washed with diluted hydrochloric acid to remove a Li salt and a triethylamine salt. Further, this was neutralized by a sodium carbonate aqueous solution and then washed with water. The organic phase was dried on anhydrous magnesium sulfate, and then the solvent was distilled off by means of an evaporator to obtain 38 g of a crude reaction product. n-Hexane 100 ml was added to the crude reaction product, and the solution was cooled while stirring to remove deposited 2-cyanomethyl-2-adamantanol by filtration. Activated carbon was added to the n-hexane solution to confirm that the solution became colorless, and it was filtered off. Then, the solvent was distilled off by means of an evaporator to obtain a colorless liquid. It was analyzed by gas chromatography to confirm that the intended product having a purity of 97.0% was obtained at a yield of 35.0 g. The respective data of $^1$H-NMR, $^{13}$C-NMR and GC-MS are shown below.

Nuclear Magnetic Resonance Spectral Method (NMR): CDCl$_3$ $^1$H-NMR (500 MHz): 1.66 (d, J=13.0 Hz, 2H), 1.74 to 1.78 (m, 4H), 1.82 to 1.87 (m, 4H), 1.96 (s, 3H, a), 2.40 (d, J =12.3 Hz, 2H), 2.55 (s, 2H), 3.41 (s, 2H, f), 5.60 (s, 1H, b$^1$), 6.15 (s, 1H, b$^2$)

$^{13}$C-NMR (127 MHz): 18.39 (a), 23.39 (f), 26.35 (k or l), 26.72 (l or k), 32.69 (i or j), 34.00 (j or i), 37.68 (m), 83.99 (e), 116.60 (g), 126.15 (b), 136.72 (c), 166.39 (d)

Gas chromatography mass spectrometry (GC-MS): EI 259 (M$^+$, 4%), 173 (92%), 133 (75%), 91 (100%), 69 (49%)

Example 2

Synthesis of 2-(1-cyanoethyl)-2-adamantyl Methacrylate Represented by a Structural Formula

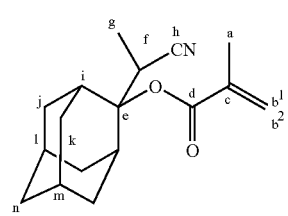

A glass reactor of 500 ml which was equipped with a stirrer and dropping funnel was charged with 100 ml of dried tetrahydrofuran and 25 ml of hexamethylphosphoric acid triamide (HMPA), and it was cooled (−50° C.) on a dry ice/isopropanol bath and then charged with a solution obtained by dissolving 22.2 g (148 millimole) of adamantanone (Adamantanone, manufactured by Idemitsu Petrochemical Co., Ltd.) in 100 ml of tetrahydrofuran and 8.6 ml (163 millimole) of propionitrile. A lithium diisopropylamide solution (1.8M) 90 ml (162 millimole) was dropwise added thereto in 30 minutes. After finishing dropwise adding, the temperature was slowly elevated up to 0° C. This reaction liquid was dropwise added in 30 minutes to a solution of 47 ml (318 millimole) of methacrylic anhydride, 45 ml (320 millimole) of dried triethylamine and 100 ml of dried tetrahydrofuran while the solution was cooled to 0° C. on an ice and water bath. After further stirred at 0° C. for 30 minutes, 200 ml of water and 300 ml of diethyl ether were added thereto and stirred. This solution was transferred into a separating funnel of 2 liter to remove an aqueous phase, and then an organic phase was washed with diluted hydrochloric acid to remove a Li salt and a triethylamine salt. Further, this was neutralized by a sodium carbonate aqueous solution and then washed with water. The organic phase was dried on anhydrous magnesium sulfate, and then the solvent was distilled off by means of an evaporator to obtain 40 g of a crude reaction product. n-Hexane 100 ml was added to the crude reaction product, and the solution was cooled while stirring to remove deposited 2-(1-cyanoethyl)-2-adamantanol by filtration. Activated carbon was added to the n-hexane solution to confirm that the solution became colorless, and it was filtered off. Then, the solvent was distilled off by means of an evaporator to obtain 34.0 g of a colorless solid matter. It was analyzed by gas chromatography to confirm that the intended product having a purity of 95.1% was obtained. The respective data of $^1$H-NMR, $^{13}$C-NMR and GC-MS are shown below.

Nuclear Magnetic Resonance Spectral Method (NMR): CDCl$_3$ $^1$H-NMR (500 MHz): 1.33 (d, J=7.0 Hz, 3H, g), 1.66 to 1.72 (m, 2H), 1.76 to 1.90 (m, 8H), 1.98 (s, 3H, a), 2.05 to 2.07 (m, 1H), 2.42 (d, J=2.3 Hz, 1H), 2.88 (d, J=1.6 Hz, 1H), 3.52 (q, J=7.0 Hz, 1H, f), 5.59 (q, J=1.5 Hz, b$^1$), 6.16 (s, 1H, b$^2$)

$^{13}$C-NMR (127 MHz): 12.80 (g), 18.55 (a), 26.37 (f or i or l or m), 26.49 (f or i or l or m), 31.11 (f or i or l or m), 32.64 (f or i or l or m), 33.19 (j or k or n), 33.23 (j or k or n), 33.74 (j or k or n), 33.98 (f or i or l or m), 34.54 (j or k or n), 37.79 (j or k or n), 85.83 (e), 120.49 (h)

Gas chromatography mass spectrometry (GC-MS): EI 273 (M$^+$, 0.6%), 187 (87%), 145 (30%), 133 (48%), 105 (24%), 91 (92%), 69 (100%)

Examples 3 and 4 and Comparative Examples 1 and 2

The compounds synthesized in Examples 1 and 2 were evaluated for an acid decomposability by the following procedure. The results thereof are shown in Table 1.

(1) A sample (120 μ mole) for evaluation was put into a sample tube for NMR and dissolved in 0.61 ml of DMSO-d6 (heavy hydrogen dimethyl sulfoxide).

(2) Trifluoromethanesulfonic acid 5.40 μ liter (61 μ mole) was added thereto. At this point of time, the base concentration was 200 μ mole/ml, and the acid concentration was 100 μ mole/ml.

(3) This sample tube was set to NMR to start decomposition reaction at 100° C.

(4) $^1$H-NMR was measured one hour later to calculate a decomposition rate of the sample.

TABLE 1

| | Sample | Amount (mg) | Decomposition Rate (%) 1 hr |
|---|---|---|---|
| Example 3 | 2-Cyanomethyl-2-adamantyl methacrylate | 31.1 | 0.0 |
| Example 4 | 2-(1-Cyanoethyl)-2-adamantyl methacrylate | 32.8 | 0.0 |
| Comparative Example 1 | 2-Methyl-2-adamantyl methacrylate*$^1$ | 28.6 | 52.4 |
| Comparative Example 2 | 2-Ethyl-2-adamantyl methacrylate*$^2$ | 29.5 | 80.0 |

*$^1$Adamantate MM, manufactured by Idemitsu Petrochemical Co., Ltd.
*$^2$Adamantate EM, manufactured by Idemitsu Petrochemical Co., Ltd.

As can be found from the results shown in Table 1, decomposition by acid was not observed in the compounds containing a cyano group.

INDUSTRIAL APPLICABILITY

The adamantane derivatives of the present invention are novel nitrile group-containing adamantyl (meth)acrylates and useful as a monomer for functional resins such as a photosensitive resin in the photolithograph field, and it is stable against an acid-generating agent when used for a photoresist material.

What is claimed is:

1. An adamantane derivative characterized by having a structure represented by Formula (I):

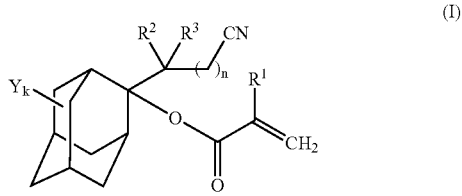

wherein R$^1$ represents a hydrogen atom, methyl or trifluoromethyl; Y represents an alkyl group having 1 to 10 carbon atoms, a halogen atom, a hydroxyl group or =O formed by combining two Y, and plural Y may be the same or different; R$^2$ and R$^3$ represent a hydrogen atom or an alkyl group having 1 to 10 carbon atoms; k represents an integer of 0 to 14; n represents an integer of 0 to 3; and R$^2$ and R$^3$ may be the same or different.

2. The adamantane derivative as described in claim 1, wherein n is 0 in Formula (I) described above.

3. A production process for an adamantane derivative represented by Formula (I-a):

(I-a)

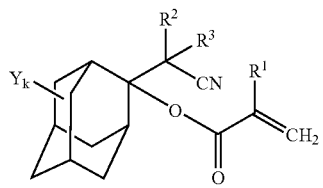

(wherein $R^1$, $R^2$, $R^3$, Y and k are the same as those described above), characterized by reacting adamantanes represented by Formula (II):

(II)

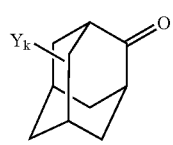

(wherein Y represents an alkyl group having 1 to 10 carbon atoms, a halogen atom, a hydroxyl group or =O formed by combining two Y; k represents an integer of 0 to 14; and plural Y may be the same or different) with a nitrile compound represented by Formula (III):

(III)

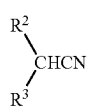

(wherein $R^2$ and $R^3$ represent a hydrogen atom or an alkyl group having 1 to 10 carbon atoms; and $R^2$ and $R^3$ may be the same or different) in the presence of a base and then with acid halide or acid anhydride of (meth)acrylic acids represented by Formula (IV):

(IV)

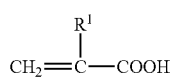

(wherein $R^1$ represents a hydrogen atom, methyl or trifluoromethyl).

4. A production process for an adamantane derivative represented by Formula (I):

(I)

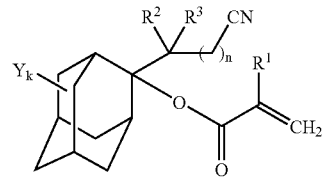

(wherein $R^1$, $R^2$, $R^3$, Y, k and n are the same as those described above), characterized by subjecting adamantanes represented by Formula (II):

(II)

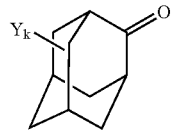

(wherein Y represents an alkyl group having 1 to 10 carbon atoms, a halogen atom, a hydroxyl group or =O formed by combining two Y; k represents an integer of 0 to 14; and plural Y may be the same or different) to Grignard reaction with a nitrile compound represented by Formula (V):

(V)

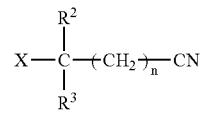

(wherein $R^2$ and $R^3$ represent a hydrogen atom or an alkyl group having 1 to 10 carbon atoms; X represents a halogen atom; n represents an integer of 0 to 3; and $R^2$ and $R^3$ may be the same or different) and then reacting it with acid halide or acid anhydride of (meth)acrylic acids represented by Formula (IV):

(IV)

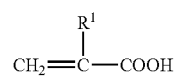

(wherein $R^1$ represents a hydrogen atom, methyl or trifluoromethyl).

5. The production process for an adamantane derivative as described in claim 4, wherein n is 0 in the nitrile compound represented by Formula (V).

* * * * *